US00PP23006P3

(12) United States Plant Patent
Harris

(10) Patent No.: US PP23,006 P3
(45) Date of Patent: Sep. 4, 2012

(54) AZALEA PLANT NAMED 'MNIHAR012'

(50) Latin Name: ***Rhododendron* sp.**
Varietal Denomination: MNIHAR012

(75) Inventor: James O. Harris, Lawrenceville, GA (US); Ella Ruth Harris, legal representative, Lawrenceville, GA (US)

(73) Assignee: Ella Ruth Harris, Lawrenceville, GA (US), Executor of the Estate of James O. Harris ( * ) Notice: Subject to any disclaimer, the term of this patent is extended or adjusted under 35 U.S.C. 154(b) by 142 days.

(21) Appl. No.: 12/807,055

(22) Filed: Aug. 25, 2010

(65) Prior Publication Data

US 2012/0054928 P1 Mar. 1, 2012

(51) Int. Cl.
*A01H 5/00* (2006.01)

(52) U.S. Cl. ..... Plt./238

(58) Field of Classification Search ..... Plt./238
See application file for complete search history.

*Primary Examiner* — Kent L Bell

(74) *Attorney, Agent, or Firm* — Jondle & Associates, P.C.

(57) ABSTRACT

A new and distinct variety of Azalea plant with spring, late summer and fall blooming, attractive, showy, semi-double, hose-in-hose flowers, easily propagated by semi-hardwood cuttings in late spring through summer, moderate growth rate under normal fertilization and moisture conditions; globose and freely-branching in habit, grows well in containers, thrives in shade or sun and is hardy in Zone 6, is disclosed.

2 Drawing Sheets

Genus and species: *Rhododendron* sp.
Variety denomination: 'MNIHAR012'.

BACKGROUND OF THE NEW PLANT

The present invention is a new and distinct variety of evergreen Azalea of the genus *Rhododendron*. This new Azalea, hereinafter referred to as 'MNIHAR012', was discovered in 2003 in Lawrenceville, Ga. 'MNIHAR012' originated from a planned cross hybridization in 1999 between the female azalea plant 'Conlec' (U.S. Plant Pat. No. 10,580) and the male azalea plant 'September Morn' (unpatented) in a controlled environment in Lawrenceville, Ga. The present invention has a blooming period in spring, late summer and fall, an upright, globose, and dense growth habit, and cold hardiness.

The new plant was first propagated via semi-hardwood cuttings in 2003 in Dearing, Ga. and has been asexually reproduced repeatedly by semi-hardwood cuttings in Dearing, Ga. for over seven years. 'MNIHAR012' has been found to retain its distinctive characteristics through successive asexual propagations via semi-hardwood cuttings.

'MNIHAR012' has not been made publicly available or sold more than one year prior to the filing date of this application.

SUMMARY OF THE INVENTION

The following are the most outstanding and distinguishing characteristics of this new cultivar when grown under normal horticultural practices in Dearing, Ga.

1. Spring, late summer and fall blooming;
2. Attractive, showy, purple colored flowers;
3. Numerous semi-double hose-in-hose flowers;
4. Easily propagated by semi-hardwood cuttings in late spring through summer;
5. Moderate growth rate under normal fertilization and moisture conditions;
6. Upright, globose, and dense growth habit;

7. Grows well in containers;
8. Thrives in shade or sun; and
9. Hardy in Zone 6.

DESCRIPTION OF THE PHOTOGRAPHS

This new Azalea hybrid variety is illustrated by the accompanying photographs which show buds, flowers, immature foliage and mature foliage. The colors shown are as true as can be reasonably obtained by conventional photographic means. The photographs are of 4-year-old plants grown in filtered shade and full sun in September in 2009 in Dearing, Ga.

DETAILED BOTANICAL DESCRIPTION OF THE NEW PLANT

Figure 1:
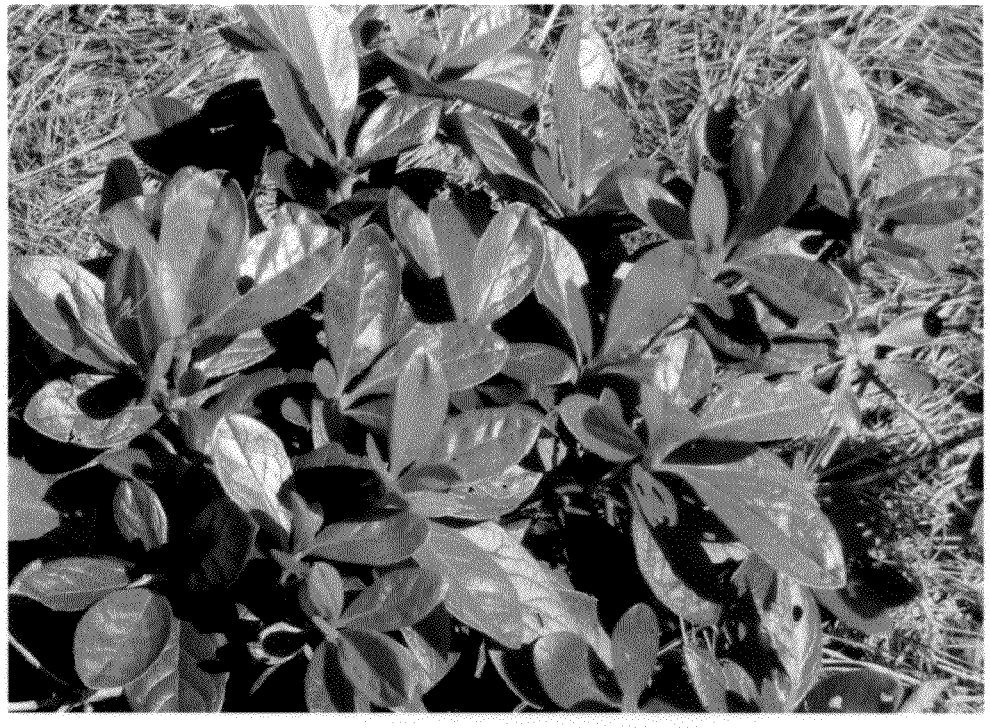
FIG. 1 is a close-up showing mature foliage.
Figure 2:
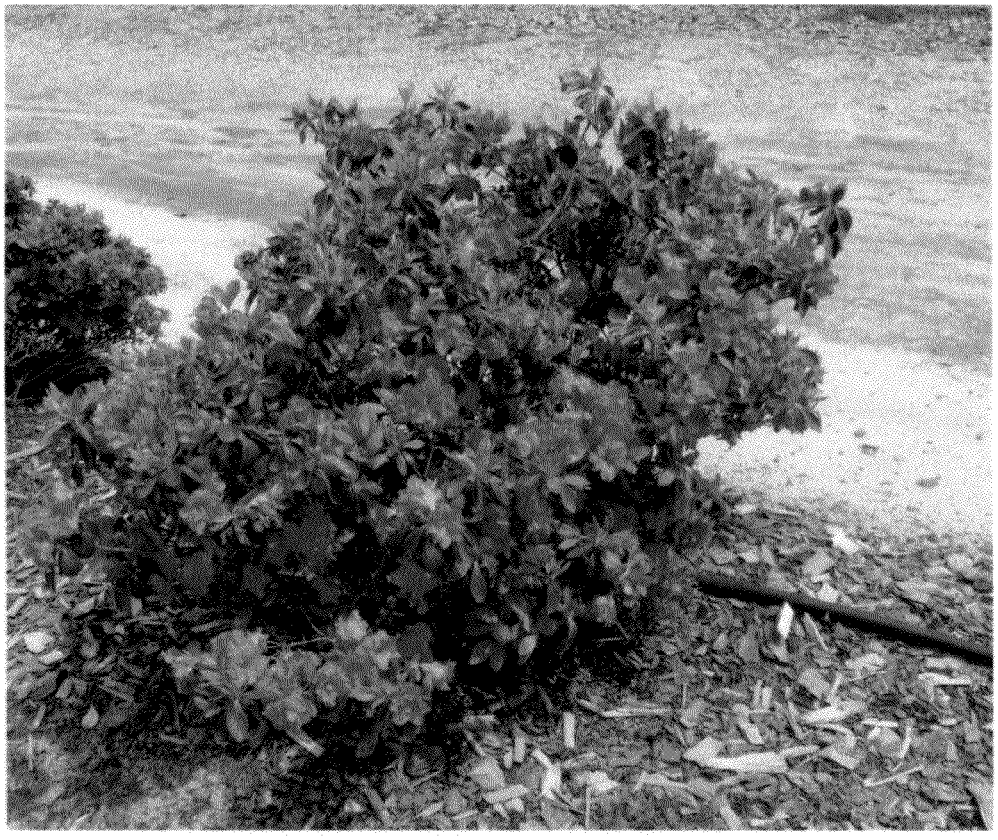
FIG. 2 shows mature foliage and growth habit of a five year old plant.
Figure 3:
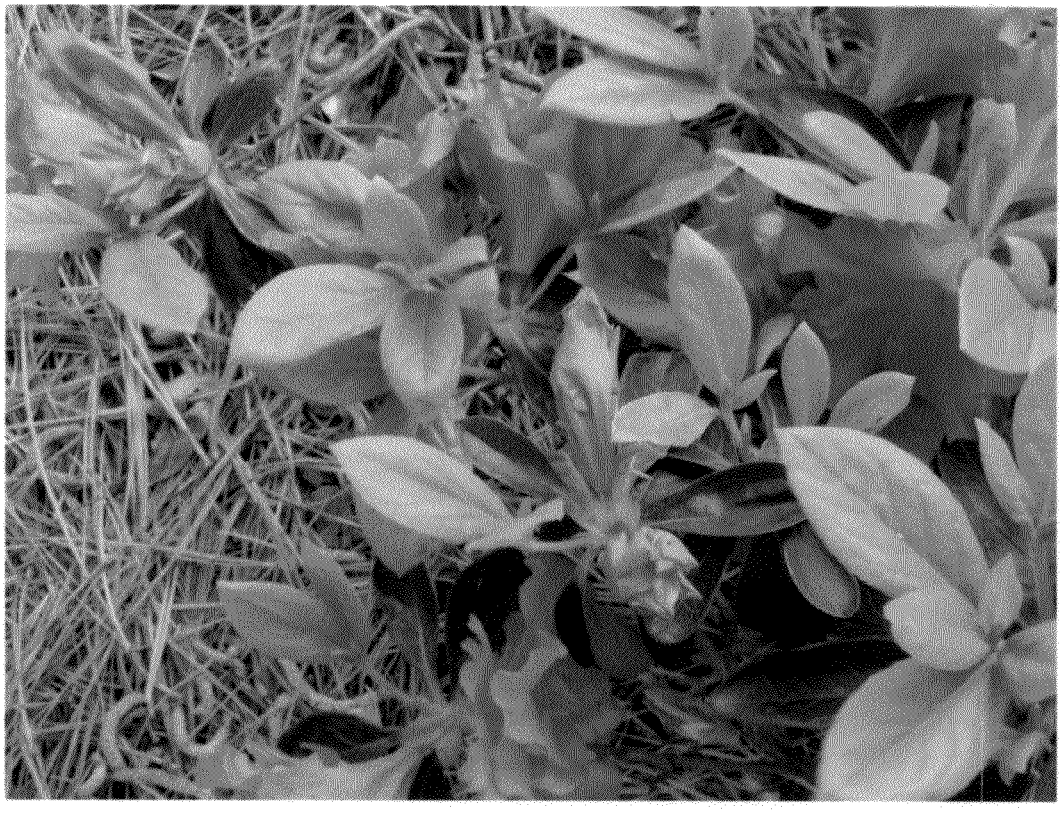
FIG. 3 is a close-up showing flower buds and immature foliage.
Figure 4:
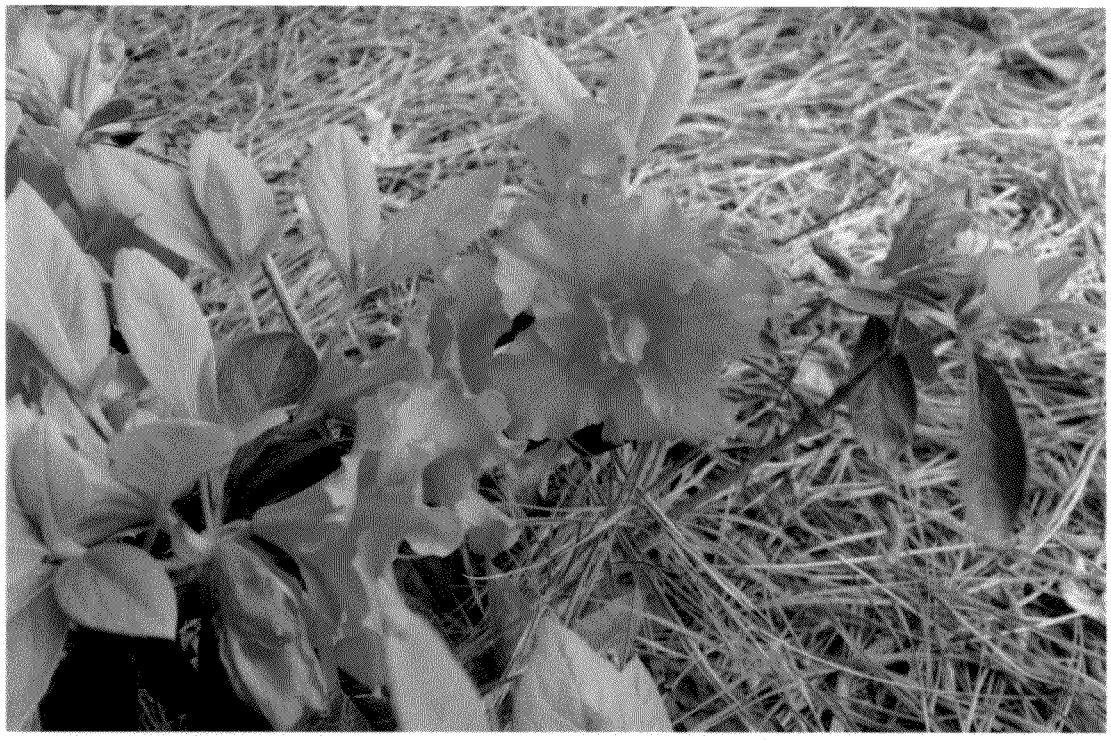
FIG. 4 is a close-up showing flower size, form, and color.

The following is a detailed description of the new variety of Azalea based on observations made of 4-year-old plants grown in three-gallon containers according to wholesale commercial production conditions, under full-sun and in an evaluation bed under semi-shade conditions in Dearing, Ga. in the spring, summer, and fall seasons of 2009. The colors of the various plant parts are detailed with reference to The Royal Horticultural Society Colour Chart (2001).

Classification:

*Family*.—Ericaceae.
*Species*.—*Rhododendron* sp.
*Common Name*.—Azalea.
*Commercial Name*.—'MNIHAR012'.

Parentage:

*Female parent*.—The azalea plant 'Conlec' (U.S. Plant Pat. No. 10,580).

*Male parent*.—The azalea plant 'September Morn' (unpatented).

Growth:

*Form*.—Upright, globose, dense.

*Texture*.—Medium.

*Height*.—91.44 cm to 106.68 cm.

*Width*.—121.92 cm to 152.4 cm.

*Growth habit*.—Freely-branching; dense and compact in nature.

*Growth rate*.—Moderate growth rate under normal fertilization and moisture conditions. In a period of five years from a rooted cutting the plant reaches a height of 63.5 cm and a spread of 96.52 cm. The growth rate is normally about 6.5 cm per year; the plant reaches a height of 91.44 cm to 106.68 cm at maturity while maintaining a dense habit due to the abundant branch development.

*Spring growth*.—The date of initial spring growth is April 3, followed by continuous growth through fall.

*Life cycle*.—Perennial and evergreen.

Leaves:

*Arrangement*.—Alternate, simple, pubescent, and evergreen.

*Shape*.—Elliptic to obovate.

*Apex*.—Acute.

*Base*.—Acute.

*Margin*.—Entire.

*Length*.—4.4 cm.

*Width*.—1.4 cm.

*Venation pattern*.—Pinnate; the mid-veins and laterals are impressed on the upper surface and the prominent on the lower surface.

*Immature leaf*.—Upper surface: Color: Matte, RHS 144A (yellow-green) to RHS N144A (yellow-green) with RHS 45A (red) on edge and apex. Pubescence: Strigose and scabrous concentrated along midrib and margin. Pubescence color: RHS N155A (white) to RHS 165C (greyed-orange). Lower surface: Color: Matte, RHS 146C (yellow-green). Pubescence: Strigose and scabrous concentrated along midrib and margin. Pubescence color: RHS N155A (white).

*Mature leaf*.—Upper surface: Color: Semi-glossy, RHS 147A (yellow-green). Pubescence: Strigose, color is RHS 164D (grey-orange). Lower surface: Color: Matte, RHS 146A (yellow-green). Pubescence: Scabrous, strigose along midrib. Pubescence color: RHS 159A (orange-white).

*Petiole*.—Length: 1.3 cm. Diameter: 0.2 cm by 0.1 cm. Pubescence: Strigose with some villous. Length: 0.1 cm. Color: Immature: RHS N155D (white). Mature: RHS 164C (greyed-orange). Color: Immature: RHS 145A (yellow-green). Mature: RHS 145C (yellow-green) with areas of RHS N144A (yellow-green) and 145B (yellow-green).

Stems:

*Form*.—Densely branched at buds.

*Young stems* (*1-year-old and younger*).—Color: RHS 145A (yellow-green). Pubescence: Hispid and strigose RHS N155A (white) to RHS 164C (greyed-orange).

*Second-year stems*.—Color: RHS 199A (grey-brown) and N200B (brown). Pubescence: Strigose. Pubescence color: RHS 199C (grey-brown) in color. Length: 6.5 cm on average. Diameter: 0.3 cm. Pith: Solid and uniform. Internode length: Average 0.8 cm.

Flower buds:

*Arrangement and form*.—Tight; borne in groups of two or three, sheathed by one to three modified leaf bracts. Length: average 2 cm. Width: 0.9 cm. Color: RHS 147A (yellow-green).

*Shape*.—Ovate.

*Apex*.—Acute.

*Base*.—Rounded.

*Length* (*at tight bud*).—1.3 cm.

*Diameter* (*at tight bud*).—0.6 cm.

*Color* (*of scales*).—Immature: RHS 145D (yellow-green). Mature: RHS 145A (yellow-green).

*Texture*.—Pubescent; strigose pubescence. Pubescence color: RHS 164B (greyed-orange).

*Pedicel*.—Length: 0.8 cm. Diameter: 0.175 cm. Texture: Pubescent, strigose and villous pubescence. Pubescence color: RHS N155A (white). Color: RHS 145A (yellow-green) to RHS 58A (red-purple).

*Calyx*.—Not present modified into bottom row of petals in hose-in-hose flower form.

Flowers:

*Type*.—Perfect, Semi-double hose-in-hose flowers.

*Shape*.—Open funnel-shaped.

*Flowering habit and period*.—Borne on the current season's growth; three weeks beginning in late March until mid April in Dearing, Ga.; flowering resumes in late July and continues until frost which can be as late as November or December.

*Lastingness of flowers on the plant*.—4 to 6 days in the sun; 4 to 7 days in the shade.

*Fragrance*.—Absent.

*Diameter*.—6.3 cm.

*Depth*.—6.3 cm.

*Petals*.—Quantity per flower and arrangement: Two layers of 5 imbricate petals that are fused at the base and remain fused up to 1.8 cm from base. Shape: Obovate. Apex: Rounded, with some retuse. Base: Fused. Margin: Entire, undulate. Texture (both upper and lower surfaces): Glabrous. Length (of petals without spots): 3.8 cm. Width (of petals without spots): 2.5 cm. Color: Upper surfaces: RHS 64D (red-purple). Lower surfaces: RHS 68B (red-purple) with areas of RHS 65B (red-purple) around the midrib; Color of the spots on the upper surface of the petals is RHS 58A (red-purple); spots are not visible on the lower surface of the petals.

Reproductive parts:

*Pistil*.—Quantity and form: Single, non-petaloid. Length: 3.2 cm. Diameter: 0.075 cm. Stigma: Color: RHS 46A (red). Diameter: 0.15 cm. Style color: RHS 51B (red). Ovary: Pubescent, strigose with 5 locules. Color: RHS N155A (white).

*Stamens*.—Number: 8 to 9 per flower; non-petaloid with some petaloid. Length: 1.3 cm to 3.2 cm. Color: RHS 51B (red) to RHS 11C (yellow) at the base. Anther: Length: 0.15 cm. Width: 0.1 cm. Color: RHS 65D (red-purple) with areas of RHS N79B (purple). Pollen: Sparse. Color: RHS 155D (white).

Fruit:

*Maturity*.—The capsule matures in about 6 months in Dearing, Ga. and the fruit set is low and contains about 0 to 200 non-winged seeds.

*Length.*—0.5 cm.
*Width.*—0.3 cm.
*Color.*—RHS 146B (yellow-green).

CULTURE

'MNIHAR012' grows well in a wide range of conditions and tolerates sun to shade. 'MNIHAR012' prefers moist, well-drained soil that is rich in organic matter and responds well to mulching and medium applications of fertilizer. 'MNIHAR012' does best in soil with a pH of 5.0 to 5.5 and is propagated with semi-hardwood cuttings in late spring through the summer. Azaleas root in five to six weeks with a high percentage of rooting (80% plus). Tissue culture is also an effective means of propagation for azaleas.

DISEASES AND INSECTS

Lace bugs, root weevils, and spider mites can be a problem. Fungal and bacterial pathogens have not been observed, but no resistance testing has been performed and no claim to abnormal resistance to pathogens can be made.

COMPARISON WITH PARENTAL AND COMMERCIAL VARIEITES

In Table 1, the 'MNIHAR012' is compared to parental varieties 'Conlec' (U.S. Plant Pat. No. 10,580) and 'September Morn' (unpatented) and lists the differences between the varieties.

TABLE 1

| Characteristic | 'MNIHAR012' | 'Conlec' | 'September Morn' |
|---|---|---|---|
| Plant Height (Mature) | 91.44 cm to 106.68 cm | 182.88 cm to 243.84 cm | 76.2 cm |
| Flower Diameter | 6.3 cm | 8.89 cm to 10.16 cm | 5.08 cm to 6.35 cm |
| Flower Form | Semi-double, hose-in-hose | Single | Single |
| Flower Color | Purple | Purple | Red |
| Bloom Period | Late March to Mid April and late July until frost | April and late July until frost | Early April |
| Hardy Zone | 6 | 7 | 5 |
| Stamen Number | 8 to 9 | 8 to 10 | 5 |
| Stamen Type | Petaloid and Non-petaloid | Non-petaloid | Non-Petaloid |

When 'MNIHAR012' is compared to the commercial variety 'Roblen' (U.S. Plant Pat. No. 16,248), 'MNIHAR012' has a broader growth habit with a height of 63.5 cm and a spread of 96.52 cm in five years, while 'Roblen' (U.S. Plant Pat. No. 16,248) has a height of 91.44 cm and a spread of 60.96 cm in six years. Additionally, 'MNIHAR012' produces purple flowers, while 'Roblen' has bright red flowers.

We claim:

1. A new variety of Azalea plant named 'MNIHAR012' as herein shown and described.

* * * * *